(12) United States Patent
Sanders

(10) Patent No.: US 8,449,552 B2
(45) Date of Patent: May 28, 2013

(54) SURGICAL DRILL GUIDE WITH AWL AND METHOD OF USE

(75) Inventor: Brett Sanders, Chattanooga, TN (US)

(73) Assignee: Quantum Surgical, Chattanooga, TN (US)

( * ) Notice: Subject to any disclaimer, the term of this patent is extended or adjusted under 35 U.S.C. 154(b) by 449 days.

(21) Appl. No.: 12/794,278

(22) Filed: Jun. 4, 2010

(65) Prior Publication Data

US 2010/0312249 A1 Dec. 9, 2010

Related U.S. Application Data

(60) Provisional application No. 61/184,031, filed on Jun. 4, 2009, provisional application No. 61/184,360, filed on Jun. 5, 2009.

(51) Int. Cl.
*A61B 17/17* (2006.01)
*A61B 17/90* (2006.01)

(52) U.S. Cl.
USPC .......................................... 606/96; 606/148

(58) Field of Classification Search
USPC ................. 600/229; 606/80, 96–98, 148, 228
See application file for complete search history.

(56) References Cited

U.S. PATENT DOCUMENTS

| 5,284,130 | A  | * | 2/1994 | Ratliff ............................ 600/229 |
| 5,681,333 | A  | * | 10/1997 | Burkhart et al. ............... 606/148 |
| 7,494,490 | B2 | * | 2/2009 | Justin ............................... 606/96 |
| 7,918,868 | B2 | * | 4/2011 | Marshall et al. ............... 606/144 |
| 2007/0233128 | A1 | * | 10/2007 | Schmieding et al. ........... 606/79 |
| 2010/0121375 | A1 | * | 5/2010 | Pandya ......................... 606/232 |

\* cited by examiner

*Primary Examiner* — Nicholas Woodall
*Assistant Examiner* — Larry E Waggle, Jr.
(74) *Attorney, Agent, or Firm* — Stephen J. Stark; Miller & Martin PLLC

(57) ABSTRACT

A drill guide and pin system is provided whereby a drill may be inserted through a drill sleeve into a bone portion to provide a drill bore. For some embodiments, a cooperating pin provides a pin bore which intersects the drill bore at a predetermined angle α and predetermined location relative to at least one of the drill sleeve and/or bore. The pin may have an integral catch so that when a wire is inserted through the drill bore, the catch can pull the wire through the pin bore for use in various surgical techniques. Some embodiments have an articulated arm which can lock in a fixed position in a fixed configuration and have a moveable configuration as well.

20 Claims, 5 Drawing Sheets

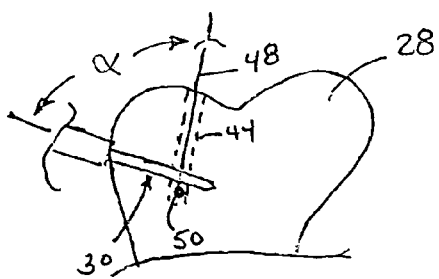
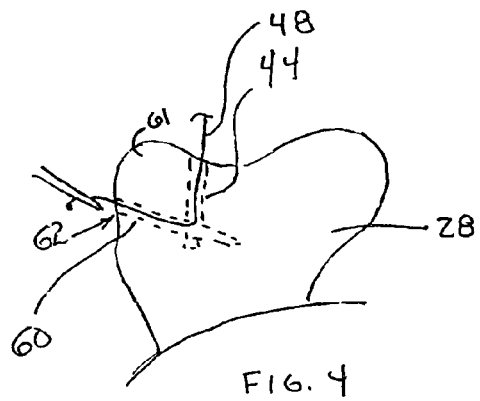
FIG. 3  FIG. 4
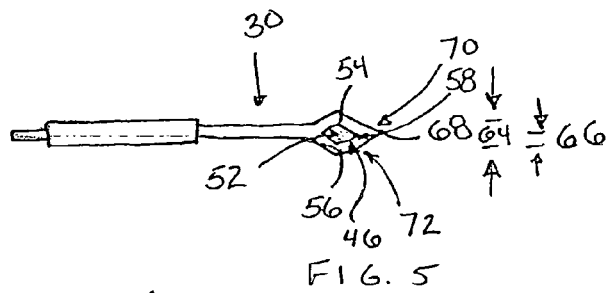
FIG. 5
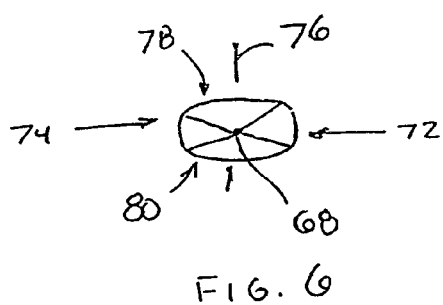
FIG. 6
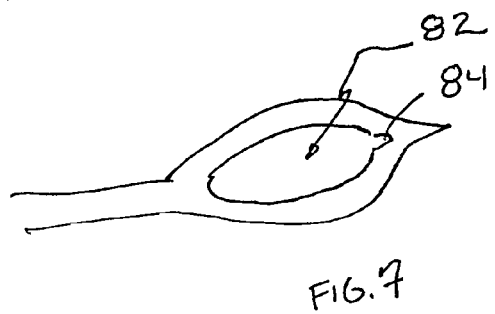
FIG. 7

US 8,449,552 B2

SURGICAL DRILL GUIDE WITH AWL AND METHOD OF USE

CLAIM OF PRIORITY

This application claims the benefit of U.S. Provisional Patent Application No. 61/184,031 filed Jun. 4, 2009 and U.S. Provisional Patent Application No. 61/184,360 filed Jun. 5, 2009.

FIELD OF THE INVENTION

The present invention relates to drill guides utilized in surgery, and more particularly to drill guides for creation of bone tunnels, and for at least some embodiments to drill guides having a catch configured to capture a wire inserted through a first bore made with a drill which allows for a surgeon or other medical personnel to run a wire through a portion of bone through the first bore and out a second bore left by retraction of the pin out of the bone and/or for at least some embodiments drill guides having at least one adjustable arm such as an articulated column which allows for a surgeon or other medical personnel to adjust the position of a pin relative to a drill guide sleeve in an efficient and easy manner, such as around non-linear anatomic structures with an ability to locate the connecting structure between the pin and sleeve at desirable positions during minimally invasive surgery.

DESCRIPTION OF RELATED ART

Drill guides are widely used in many surgical procedures. Patents such as U.S. Pat. Nos. 6,210,415, 6,342,056, 6,746,453, 6,916,323, 6,908,916, 7,166,113, 7,192,432, 7,491,206 and others such provide an ability to adjust guide sleeves in at least one of angular rotation or along usually only one of an X, Y or Z direction relative to the location of a pin relative to a drill guide for use in drilling relative to the pin. These drill guides are widely used in arthroscopic surgery to create bone tunnels for tendon/ligament repair in a minimally invasive fashion.

While these prior art devices work well for their intended purposes when drilling straight, easily accessible tunnels, they have shortcomings in certain situations. The angle between the drill guide targeting tip and the drill sleeve must generally be greater than 90 degrees, which is not possible in certain location due to anatomic constraints. Thus, when a pin is placed at a desired position relative to the bone, and after the bore is drilled, there is no easy way to run a wire through the bore in the bone so as to use to re-attach tendons or for other purposes. While an anchor could be inserted into the bore, typically only a limited number of anchors can be used at a single location in a patient. The bone surrounding anchors may become less strong, and the possibility of drilling one anchor into another would appear to cause problems for a patient. Also, anchors are expensive and may not be reimbursed by all private insurance companies or government backed programs.

U.S. Pat. No. 5,330,468 shows one technique of drilling a curved path through a shoulder because of anatomic imposed limitations on the achievable trajectory of the instruments. However, flexible drill bits are believed to be somewhat problematic in that they may not hit the intended target reproducibly due to scything. Furthermore, a flexible bit may break off within the bone also creating issues which need to be resolved by the surgeon.

Accordingly, a perceived need for an improved targeting system is believed to be necessary to facilitate the insertion of a wire through a portion of a bone with separate entry and exit points, such as to assist in connecting a tendon or ligament to bone, such as the rotator cuff at the shoulder or other appropriate location where entry points and instrument trajectories are limited due to anatomic constraints.

Furthermore, the applicant has discovered using many of these prior art devices which are often being applied to more sophisticated techniques in different body parts, that when the pin is placed at a desired position relative to the bone, upon attempting to locate the drill guide sleeve relative to the pin, the connecting structure between the pin and the drill guide often creates resistance or torque. Torque within the connecting structure can then misalign the sleeve relative to the pin. Also, the pin can scythe or cut off axis inadvertently such as by being deflected by bone surface, such as but not limited to a result of a low angle of incidence. When one runs the drill through a misaligned drill guide sleeve, then the hole does not emerge where it is anticipated by the surgeon. This can create problems or at least issues in at least some procedures. As a result of these issues, some medical procedures rely on freehanding pins orthoscopically by trial and error to achieve acceptable pin placement.

Accordingly, a perceived need for an improved drill guide is believed to be necessary.

SUMMARY OF THE INVENTION

It is a present object of at least some embodiments of the present invention to provide an improved drill guide.

It is a present object of at least some embodiments of the present invention to provide an improved drill guide, drill, and receiving awl which connect in an intraosseous location to facilitate making bone tunnels or passing sutures through bone in a minimally invasive, arthroscopic fashion.

It is another object of many embodiments of the present invention to provide a drill guide which is configured to catch a wire with a pin inserted through a first bore created with a drill and then pull the wire through a second bore created by the pin.

It is another object of at least some embodiments of the present invention to provide an improved drill guide receiving awl with a variety of tip geometries.

It is another object of many embodiments of the present invention to provide a drill guide in which multiple axes of adjustability are provided which can increase a drill guide's generalization to more than one anatomic situation.

It is another object of at least some embodiments of the present invention to provide an improved drill guide in which three dimensional adjustability of the drill guide relative to the pin is provided in at least some embodiments.

It is a further object of at least some preferred embodiments of the present invention to provide a drill guide which provides an articulated column operably coupling the pin to a guide sleeve.

In accordance with a presently preferred embodiment of the present invention, pin is located preferably proximate to, if not within, a bone of a patient such as in a shoulder, tibia or other location. With the pin at or near a desired placement, the sleeve can then be generally directed towards the pin. A hole may then be drilled with or through the sleeve. Preferably the hole is drilled through and/or by a portion of the pin, such as at a catch provided with and/or in the pin. With the first bore drilled, a wire can then be inserted into the first bore.

The pin preferably has a catch which cooperates with the wire, such as by pinching the wire at a pinch and/or otherwise retaining the wire relative to the pin at the catch. The pin is then retracted from the bone, thus leaving a second bore, while pulling the wire through the second bore. The wire can then be utilized to shuttle sutures through the bone tunnels and repair the tendons to the surface of the bone.

Furthermore, or alternatively, with a pin at or near a desired placement, the sleeve can then be generally directed towards the pin preferably by releasing an actuator normally retaining an articulated column in a rigid configuration. The plurality of joints connecting segments are then released in a released configuration which allows the sleeve to be positionable in at least two, if not three, directions (relative to X,Y,Z axes) relative to the pin. The surgeon can then generally locate the sleeve relative to the pin and then lock the actuator thereby securing an approximate position of the sleeve relative to the pin.

The guide may then be removed from the patient and the sleeve precisely aligned with or relative to the pin and then reinstalled in the desired configuration. Once again, the use of the actuator may assist in releasing the articulated column from a rigid configuration to a malleable and/or released configuration. Upon achieving the desired position, the actuator can be operated to lock the articulating column in a rigid configuration. Upon relocking the actuator, the sleeve can be precisely aligned and/or positioned relative to the pin. The rigid guide can then be installed relative to the patient with minimal, if any, torque on the connecting structure between the pin and the sleeve.

By providing an ability to adjust the position of the sleeve relative to the pin, precise placement over long distances may be more easily performed for some embodiments. Furthermore, an ability to selectively position much of the structure between the pin and sleeve can now be achieved, particularly when utilizing an articulated column embodiment. The connecting structure may be moved out of the way in at least some embodiments so that it does not obstruct other instrumentation, equipment and/or the line of sight of the surgeon when in use.

Other advantages may be experienced with further use of various embodiments of the invention as would be understood by those of ordinary skill in the art.

BRIEF DESCRIPTION OF THE DRAWINGS

The particular features and advantages of the invention as well as other objects will become apparent from the following description taken in connection with the accompanying drawings in which:

FIG. 3 is a reverse detailed plan view showing a portion of the bone shown in FIG. 1-2 with a wire inserted through a bore created by the drill and/or sleeve before being pulled back through a bore created by the pin;

FIG. 4 is a reverse detailed plan view showing a portion of the bone shown in FIGS. 1-3 with the wire inserted through a bore created by the drill and/or sleeve and pulled back through the bore created by the pin;

FIG. 5 is a top plan view of the pin shown in FIGS. 1-4;

FIG. 6 is a front plan view of the pin shown in FIGS. 1-5; and

FIG. 7 is a top plan view of a presently preferred pin target.

DETAILED DESCRIPTION OF THE PREFERRED EMBODIMENT

Figure 1:
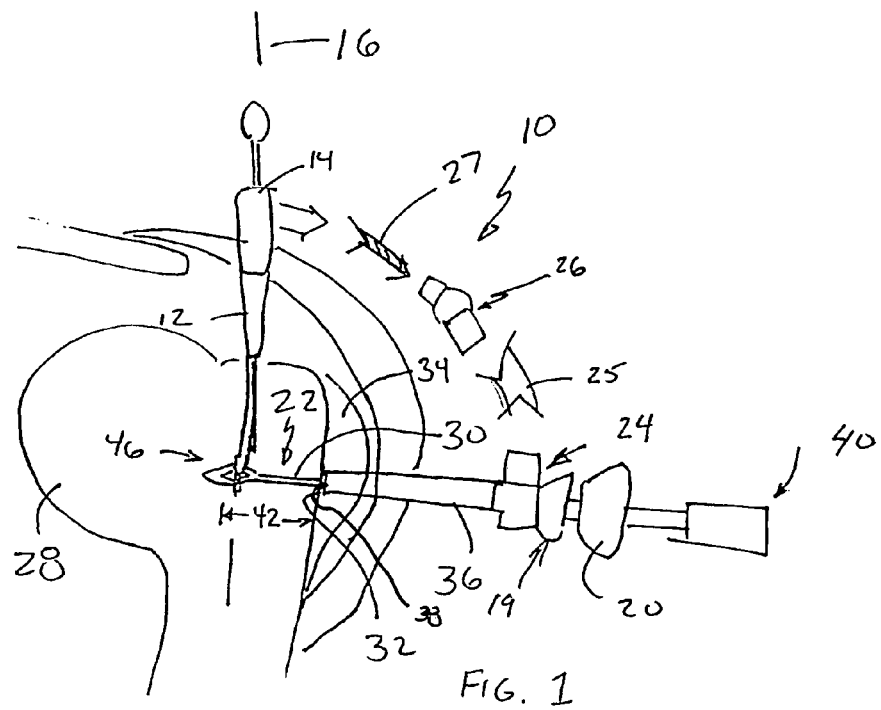
FIG. 1 of a top plan view of a presently preferred embodiment of the present invention of a surgical drill guide with an improved pin inserted into a shoulder of a patient showing a plurality of possible arm configurations.

FIG. 1 shows a drill guide 10 of a presently preferred embodiment of the present invention. The drill guide 10 has a sleeve 12 received in sleeve housing 14. Sleeve 12 may be directed along sleeve axis 16 such as with an indexing or insertion mechanism possibly including an electrical drill or other appropriate device such as a cannulated awl. U.S. Pat. No. 5,458,602, incorporated by reference, shows one style of housing 14 and sleeve 12, but there are certainly others as would be known by those of ordinary skill in the art that would work satisfactorily.

Pin 22 is shown connected to arm portion 24. Various arm portions 25,26,27 are shown with broken lines such as an articulated column arm portion 26. Further detail regarding an articulated column arm portion is discussed below. Configurations such as a flexible or otherwise movable wire 27 or other connection, or rigid, i.e. non-movable arm 25 to connect pin 22 to drill 15 and/or sleeve 12 may also be utilized. Any or all of the arm portions 25,26,27 could be utilized in various embodiments. Other arm connections as are known in the art may also be employed in other embodiments. Adjustable connections such as column 26 slides, or other mechanisms as are known in the art, may allow for positioning such as the angular position of the pin 22 relative to the bone portion 28 and/or sleeve 12 and/or provide a plurality of options as it relates to adjustment of the position of the pin 22 relative to the sleeve 12 and/or drill 15 as would be known by those of ordinary skill in the art.

Pin 22 is illustrated with shaft 30 which is shown extending into bone portion 28, such as a side of a shoulder, but could be other bone portions as is known in the art. Stop 32 is shown contacting an exterior surface 34 of the bone portion 28. Stop 32 may also be a portion of a pin sleeve 36 which may allow for extension or retraction of shaft 30 relative to sleeve 36 so as to adjust the amount of penetration of the shaft 30, at least in some embodiments such as stop plug 20 shown almost contacting shoulder 19 which would establish a maximum depth of the pin 22 into the bone 28. Other and/or additional mechanisms may be utilized with other embodiments. Drive end 40 may be useful to drive with a hammer or otherwise insert into bone portion 28. Drive end 40 may have means or mechanism such as a handle for use in pulling the shaft 30 from the bone portion 28 at a desired point in time as will be described in detail below.

With the shaft 30 of the pin 22 inserted to a desired depth 42, such as with the stop 32 contacting exterior surface 34, the sleeve 12 can then be placed against the exterior surface 34, if not already located in that position. If the sleeve 12 has cutting teeth 38, it can then start creating a hole into bone portion 28 along sleeve axis 16 as is known in the art. Otherwise, for other embodiments, a drill can be run through the drill sleeve 12 (as they are often hollow for such use) along sleeve axis 16.

Figure 2:
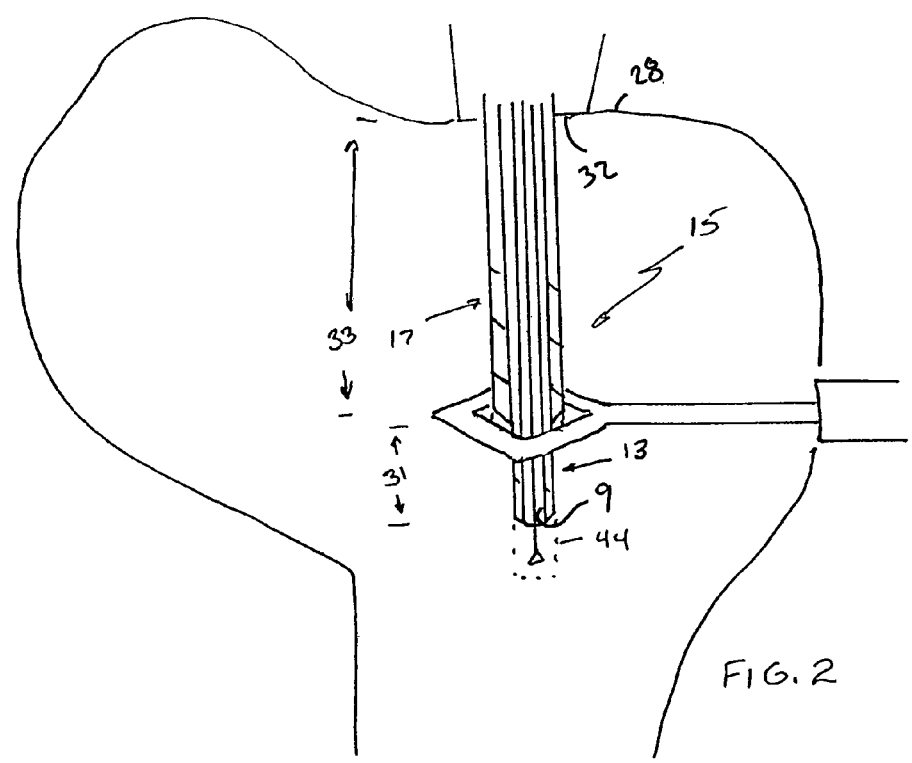
FIG. 2 is a detailed plan view showing a portion of the bone shown in FIG. 1 with the a presently preferred sleeve and/or drill drilling through the bone and past a portion of the pin.

FIG. 2 shows the embodiment of a sleeve 12 used as a cannula allowing a dual diameter drill 15 with the first diameter 17 cutting a hole past a depth 33 of a first bore 44 that the drill has cut through the bone portion 28. In fact, the second diameter 13 has passed through and/or past a catch 46 in the shaft 30 by distance 31 as will be explained in further detail below. A drill 15, if inserted through sleeve 12, would likely be located where the sleeve 12 is shown in FIG. 2 with the sleeve 12 stopping at the exterior surface 34. The contact of the first diameter 17 with the target or catch 46 may provide at least a feel of engagement for the surgeon's team.

Also, as shown in FIG. 2 a wire 48, which could be any non-rigid material having a diameter, flexibility and/or resiliency sufficient to pass through first bore 44, and a second bore (which will be described in further detail below). The illustrated wire 48 has a wire stop 50, such as a bead having a larger diameter than a diameter of the wire 48 as will be explained further below. The wire 48 is preferably fed through bore 9 in drill 15 to pass through first bore 44 in the presently preferred embodiment.

FIG. 3 shows the sleeve 12 removed, with the wire 48 remaining in position past the depth of the first bore 44 where the shaft 30 of the pin 22 passes through the first bore 44 at depth 42. In fact the wire 48 is shown in and/or beside the catch 46. The catch 46 in this embodiment has pinch 52 which is where two arms 54,56 meet at juncture 58 so that the wire 48 is contacted by both arms 54,56 and pushed towards juncture 58. In some embodiments, sharp edges internal to catch 46 may sufficiently grab wire 48 when the shaft 30 is retracted from being inserted in the bone portion 28. By providing a stop such as wire stop 50, the wire stop 50 may also be caught by the pinch 52 such as towards the juncture 58 as the arms 54,56 come together during retraction of the shaft 30.

FIG. 4 shows the wire 48, such as nitenol wire, or other appropriate material, being pulled through second bore 60 which is left in the bone portion 28 at a portion of the location where the shaft 30 was inserted into the bone portion 28. With the wire 48 directed through both the first and second bores 44,60, the surgeon and/or assistants will now have an ability to suture to tendons and secure them with the wire 48 and/or other structure to the bone portion 28. The ability to run the wire through the bone portion 28 is believed to be novel. Other uses for the wire 48 once through the bores 48,60 will be understood by those of ordinary skill in the art.

The angle shown between the sleeve first bore 44 and the second bore 60 is illustrated at about ninety degrees. It will be understood that angle α could be anything from about twenty degrees up to about 170 degrees. Factors affecting the amount of angle include the amount of bone material left remaining to provide sufficient strength to retain wire 48 to keep from breaking through corner 61 illustrated in FIG. 4 which could limit the range on the lower end of the range. On the higher end of the range, once one gets past 170 degrees, it would likely be much easier to just drill a straight hole through the bone. In practice, it is estimated that most bores 44,60 will be oriented at angles α of at least about 30 degrees, if not 45 degrees, to about 135 or about 150 degrees. Of course, ninety degree angles α as illustrated are expected to be particularly common in many applications.

The guide 10 is also believed to be novel in that the applicant is unaware of any attempts to provide a catch 46 as a portion of a pin 22. Of course other pin embodiments may take other forms, including, but not limited to moving arms 54,56, hooks or other structures configured to at least temporarily grab and retain the wire 48 for a sufficient length of time to pull the wire 48 through the second bore 60. In fact, in some alternatively preferred embodiments, the surgeon and/or assistant may be able to direct a hook having a smaller diameter shaft than pin shaft 30 illustrated through the second bore 60 after removing the shaft 30 to then pull a wire 48 from bore entrance 62 illustrated in FIG. 4.

FIG. 7 shows a presently preferred catch embodiment showing catch 82 in the form of an elliptical shape, although other shapes in other embodiments could be employed as well. A notch 84 is useful in many embodiments to provide a pinch location to grab the wire 48 when inserted. An elliptical cross section may be helpful to accommodate a wider range of angular relationships between the drill 15 and the target or catch 82 as the drill could pass through easier at some angular relationships as compared to the diamond configuration of target 46. However, both targets 46,82 work well for their intended uses.

Catch 46 is illustrated with a diamond shaped cross section as seen in FIG. 5 of a presently preferred embodiment, but other embodiments may employ other shapes. Also, a width 64 of the shaft 30 at the catch 46 is illustrated as being wider than a width 66 along other portions of shaft 30 in the presently preferred embodiments, but this need not be the case for all embodiments.

Shaft 30 preferably has point 68 at end 70 of shaft 30 to facilitate driving the shaft 30 into the bone portion 28. Arms 54,56 may have edges on sides 72, 74 which thicken toward a center-line 76 of shaft 30 to assist in driving the shaft 30 into the bone as is shown in FIG. 6 such as along sides 72,74 and/or top and bottom 78,80.

Figure 8A:
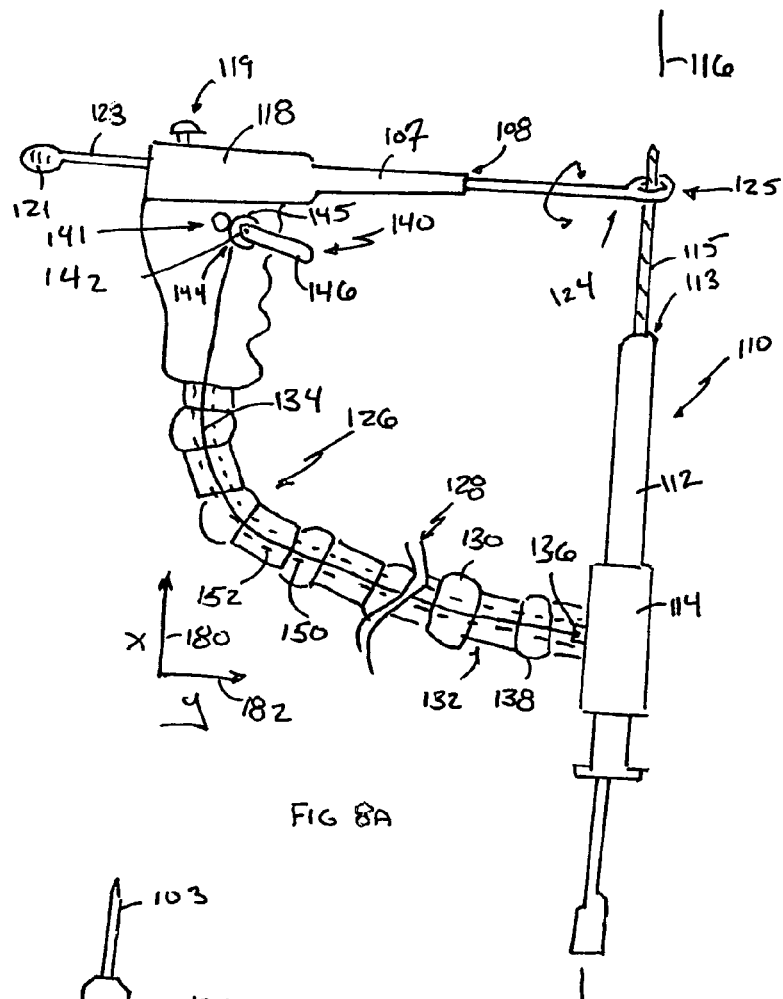
FIG. 8A is a side plan view of the presently preferred embodiment of the present invention of a surgical drill guide.

FIG. 8A shows a drill guide 110 of a presently preferred embodiment and/or alternatively preferred embodiment of the present invention. The drill guide 110 has a sleeve 112 received in sleeve housing 114 which may provide a double cannulation for applying drill pin 115 flush with bone. End 113 of sleeve 112 may contact the bone in such an arrangement. In alternatively preferred embodiments, end 113 may have serrated edges to provide a drill surface for cutting into bone such as is shown in U.S. Pat. No. 5,458,602. Sleeve 112 is preferably removably connected to sleeve housing 114.

Figure 8B:
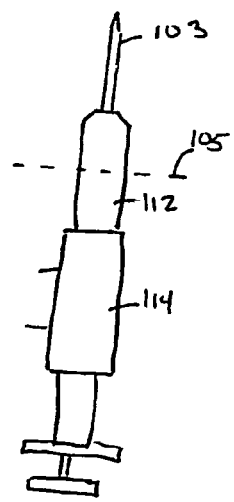
FIG. 8B is a portion of the guide shown in FIG. 8A with a blunt tipped obturator attached.

FIG. 8B shows the sleeve housing 114 receiving the blunt tip obturator 113 which could be could be utilized to penetrate muscle such as through a minimal stab incision. The obturator 113 is normally then removed from the sleeve 112 which is normally an inner cannula. The end 113 can rest on bone at a desired angle. The drill 115 can then advance through an internal orifice of sleeve 112 (inner cannula) which also passes through housing 114 (possibly an outer cannula) as would be understood by one of ordinary skill in the art.

Dotted line 105 as shown in FIG. 8B is used to represent a position the sleeve 112 could penetrate the body of a patient. One of ordinary skill in the art would understand that variable length or depth inside the body can be achieved with the sleeve 112 and/or the obturator 103 or drill 115. The sleeve housing 114 may provide an outer cannulation which is preferably attached to the remainder of drill guide outside the body in the preferred embodiment. Other embodiments may have other connections.

Sleeve 112 and/or drill pin 115 may be directed along sleeve axis 116. Drill pin 115 is then operable as drill pins are known to be operated by those of ordinary skill in the art such as by connecting an electric or other drill (not shown) to operator 19 or otherwise.

Pin target 125 on shaft 124 may be selectively positionable relative to housing 118. Locking mechanism, such as a threaded screw 119, may assist in securing pin target 125 and/or shaft 124 at a desired location. Extension 107 may end at stop 108 or other location, if utilized, in other embodiments.

In more sophisticated embodiments, the grip 121 may be pulled to unlock the shaft 124 and then grip 121 may be twisted to position the shaft 124 and/or target 125. The shaft 124 may cooperate with a threaded shaft 123 connected to the grip 121 for such capability. Of course, other mechanisms as are known in the art could be employed to provide such a capability as well as others.

Alternatively, the housing 118 may be utilized like as a cannula or otherwise so that pin shaft 124 may be placed relative to bone to be drilled as will be shown in other figures and described. Housings 114 are believed to be relatively well known in the art.

However, at least one thing that is not believed to be well known in the art is the ability to locate a pin shaft 124 and/or pin target 125 in three dimensions relative to the sleeve 112. Of course, other contemplated embodiments could provide for two dimensional positioning and will be discussed in further detail below.

Intermediate the pin shaft 124 and the sleeve 112 is preferably at least one articulated column 126. Column 126 is shown with broken lines 128 for purposes of illustrating that the length could selected by the manufacturer. Longer lengths may be desirable for some procedures, shorter lengths for others.

Articulated column 126 may be constructed of joints 130 and connecting segments 132. Normally, a wire 134 or other structure secures to a structure such as stop 136 towards one end. At least some structure such as stop 136 preferably prevents the wire 134 preferably from passing all the way through a first joint 138 when operating the actuator 140 to a rigid configuration as will be discussed below in further detail.

The other end of the cable or wire 134 is preferably connected to a actuator 140 which may be operated about pivot 142 or otherwise to move a plunger and/or connection 144 away from stop 136. In the illustrated case, connection 144 moves away from stop 136 around a circumference of gear 145. Other embodiments of mechanisms may operate similarly or dissimilarly.

The operation of the actuator 140 will be understood by those of ordinary skill in the art and may take one of many available forms in the marketplace. In the illustrated embodiment, rotating the actuator handle 146 clockwise about pivot 142 locks the actuator 140 whereby rotating counter clockwise which tends to release the actuator 140. Other embodiments may operate differently. Releasing the cable or wire 134 with the actuator 140 such as by operating release 141 tends to decrease the tension on wire 134 and therefore decreasing the tension on the joints 130 relative to the segments 132. Release 141 is shown engaging gear 145 until pushed out of engagement thereby potentially allowing gear 145 to rotate freely. Of course other systems could be employed in other embodiments.

The articulating column 126 is then in a released configuration. A released configuration at least provides an ability for an operator to move the at least two of the segments 132 relative to at least one or more joints 130 with the operation of a single actuator 40 and/or at least two joints 130 relative to one ore more segments 132. In fact, the articulating column 126 may go limp in some configurations. Some segments 132 may be restrained from movement relative to at least some joints 130 by other mechanisms (i.e., teeth and/or permanent connections) in other embodiments.

Upon moving the actuator 140 to a locked configuration, the wire 134 or other affected structure is tightened (or otherwise made rigid) thereby providing tension through the segments 132 and joints 130 re-placing the column 126 in a rigid configuration thereby securely positioning the pin 124 relative to the sleeve 112.

Figure 9:
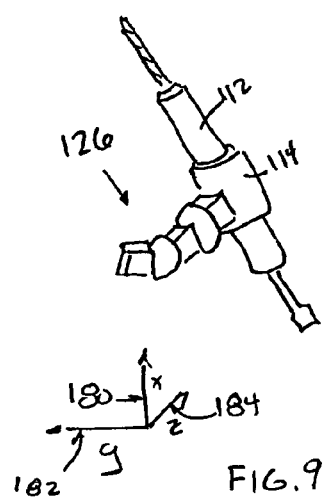
FIG. 9 is a front perspective view showing a portion of the guide shown in FIG. 8A maneuvered in x-, y-, and z-axis.

As one of ordinary skill in the art would quickly realize, by providing a relatively long length of an articulated column 126, would allow for different positions to be achievable for locating the pin 124 relative to the sleeve 112. FIG. 9 illustrates the portion of the column 126 to the right of broken lines 128 involving the twisting of the sleeve 112 into the page relative to FIG. 1 therefore showing an ability to locate the sleeve 112 along a z-axis relative to a y-axis as well as being slightly elevated on the x-axis to show three dimensional movement capability of the presently preferred embodiment. Column 126 can be positioned for such reasons as to avoid an obstacle such as a portion of an operating table or other limitation or constraint such as positioning of other equipment or line of sight, etc. Column 126 can also be positioned to provide a plurality of bores with various angles and/or paths using drill pin 115. Other considerations may come into consideration for how to position the column 126 along the x-, y- and z-axes, 180,182,184.

In order to release the column 126 from its rigid configuration, the actuator 140 is operated and put in a released configuration when the tension of cable 134 is lessened thereby allowing movement of at least some the segments 132 relative to one or some of the joints 130. Other embodiments may have segments 132 with integral joints. The figures illustrate joints 130 as balls which are received in or by segments 132. Other constructions such as those known in the prior art could be utilized for joints 130 and segments 132 as well as others.

Two dimensional or three dimensional positioning could be achieved. Instead of balls as joints 130, cylinders or other configurations could be employed for two dimensional adjustment. Furthermore, a combination of different kinds of joints 130 and/or segments 132 could be employed in various embodiments. The joints 130 such as illustrated joint 130 typically would have a bore or channel 150 which allows for the wire 134 to pass therethrough and allow for the adjustability between configurations. Furthermore, the segments 132 may engage the joints 130 at engagements as are known in the art. Segments 132 also preferably have a passage such as passage 152 to allow the wire 134 to pass through. Other tensioning members or mechanisms instead of wire 134 may be utilized in other embodiments.

Furthermore, although articulated column 126 is illustrated in the presently preferred embodiment, other constructions may allow for an ability to adjust other embodiments in three dimensions which is not believed to have been provided by prior art constructions. Two dimensional adjustment or possibly one dimensional adjustment may be possible with other embodiments. Furthermore, other embodiments may provide an ability similar to the illustrated embodiment in that an actuator 140 can allow for positioning of multiple segments 132 or joints 130, if not all or many of them, by operating a single actuator 140 when in a released configuration and then the locking of multiple joints 130 and or segments 132 with a single operation of a actuator 140 which is also believed to be novel relative to the prior art. Such a capability allows for the relative rapid positioning of a pin 124 relative to the sleeve 112 without a need to adjust connections at individual joints 130 such as with lock screws relative to sleeves provided by other prior art constructions.

Although the actuator 140 is shown connected to housing 118, it could be connected to sleeve housing 114 in other embodiments. Other locations for actuator may be utilized in still other embodiments.

Figure 10:
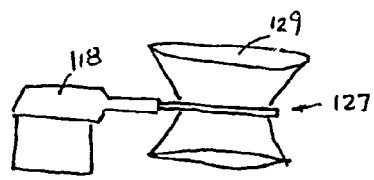
FIG. 10 is a side schematic representation of a portion of the guide shown in FIGS. 8A and 9 showing the range of possible bores with a given pin plane.
Figure 11:
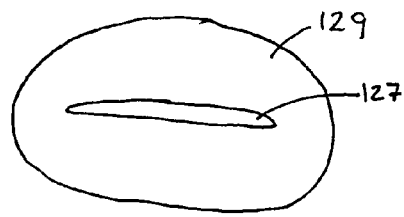
FIG. 11 is a top schematic representation of the range shown in FIG. 10.
Figure 12:
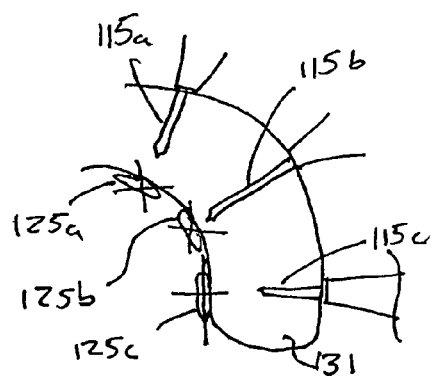
FIG. 12 is a side plan view of the guide shown in FIG. 8A showing a rotational capability of the pin of that embodiment in various positions on a bone.

FIG. 10 shows a schematic representation of possible bore locations which could be drilled with guide pin 115 based on pin shaft 124 moving in and out along a lone with the target 125 maintained in a single planar orientation (i.e., not twisted, as will be discussed below in reference to other figures). Effectively, a somewhat of a conical set of possibilities exist above and below a shaft plane 127 containing the shaft 124 for showing possible shaft location through which a drill pin 115 could penetrate target 125. This may be better visualized with reference to FIG. 11 which is a top down view of FIG. 10 with the shaft plane 127 shown below the bore range 129. A tighter cone (bore range 129) could be provided if the target 125 is constrained from movement in a direction along a length of the shaft 124.

If one provides for a rotatable shaft 124 as is provided for with the embodiment of FIG. 8A, then the bore range 129 could be rotated up to 360 degrees about the shaft 124. Such a configuration provides a possibility of bore positioning that with prior art devices would appear to be virtually impossible.

Figure 13:
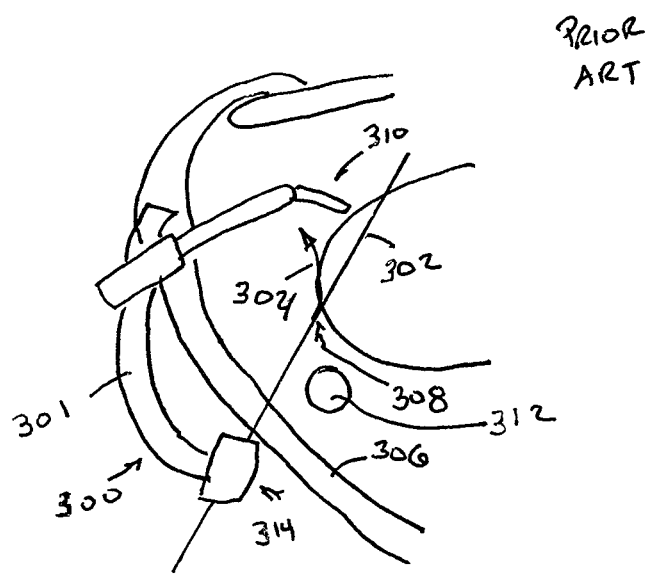
FIG. 13 is a side plan view of a prior art guide showing a tendency for a drill to scythe when contacting oblique angles of bone or not exit at a desired location because of anatomic constraints of prior art drill guides.

FIG. 13 shows one example of locating of target 125 relative to bone 131 at one of three positions, 125a, 125b, and 125c such as by rotating shaft 124 and thus target 125. Drill pin 115 is shown in three configurations 115a,115b and 115c relative to the targets 125a,125b and 125c so that the drill pin 125 will engage the target 125 as desired. The target 125 may have circular bore 133 or it may be oval shaped, or other appropriate configuration in other embodiments. One can see that the targets 125a-125c are twisted relative to one another about an axis running through perpendicularly through the page along the axes marked through each of the targets 125a, 125b and 125c.

In operation, the guide 110 can be located at appropriate location relative to the patient. Specifically, the pin 124 can be located in or at a bone or other portion of the patient and then the sleeve 112 at least somewhat directed towards the pin 124. This can be done by moving the actuator 140 so as to place the column 126 to a released configuration. When the sleeve 112 is positioned in a desired position relative to the pin 124, or visa versa, the actuator 140 can be operated so as to place the column 126 in a rigid configuration and the guide 110 can then be removed from the patient. The surgeon or other personnel can then make minor, or even possibly major, adjustments so as to align the sleeve 112 precisely relative to the pin 124 as desired by once again placing the actuator 140 in the released position making the necessary changes to position and then operating the actuator 140 so as to place the column 126 in the rigid configuration with the desired alignment between the pin 124 and the sleeve 112. The guide 110 then can be placed back relative to the patient such as with the pin 124 in the bone or otherwise and then the guide 110 will be precisely located so the sleeve 112 can precisely locate a drill 115 in a desired location so that the hole drilled utilizing the drill guide 110 will be as decided by the surgeon and unexpected locations and holes will be avoided as can occur in some operations utilizing some methodology in the prior art.

FIG. 13 shows problems with a prior art guide 300 having a rigid (and non-movable) arm 301 securely connected to at least one of the pin and drill. This guide 300 is illustrated as being restricted by anatomic constraints including muscle 306. As a result pin scythe is shown whereby instead of following path 302, any number of scything positions such as 304 and others could occur. This can result from an oblique angle occurring where the drill contacts the bone at interface 308. As one can see the guide 300 is under considerable torque as the pin target 310 is not aligned with path 302. Even if the drill were able to avoid scything and follow path 302, it would still miss the target 310. Care should normally be taken to miss nerve 312 as well.

When attempting to properly locate arm 301 or drill guide 300, the muscle 306 can block or obstruct the rotation of drill guide to a desired location. This can create a low angle of incidence for at least in some applications. Alternatively, excessive torque and/or force may be applied than is designed or planned to be applied therefore pushing the end 314 against muscle 306 or otherwise imparting such force that the drill guide 300 may be in an awkward position such that it can be become unwieldy and/or unpredictable. The end location of the path 302 may then be unpredictable.

Figure 15:
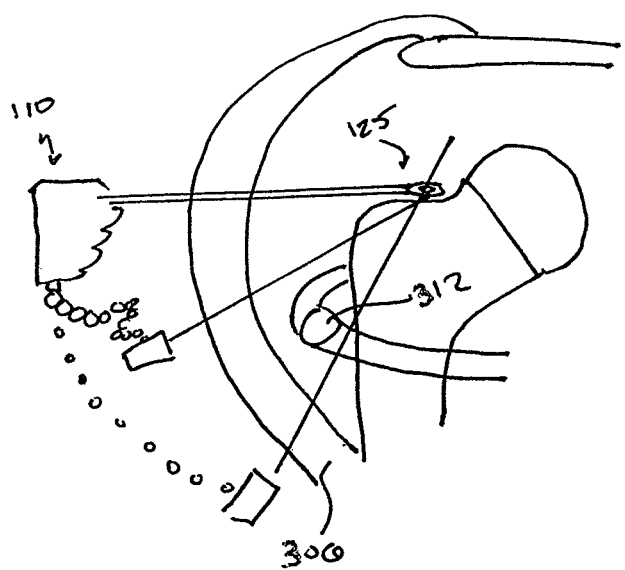
FIG. 15 is a diagrammic representation of the guide of the presently preferred embodiment overcoming prior art disadvantages.

FIG. 9 shows a diagrammic representation of correctly hitting target 125 while avoiding nerve 312 as well as other restraints such as could arise from muscle 306 and/or other issues. Still other surgery techniques may discover other advantages using the guide 110 as disclosed in the presently preferred embodiments. As one can see from FIG. 15, different positions and locations can be provided utilizing the articulating arm 126 to avoid neurovascular injury or other undesired effects.

Figure 14:
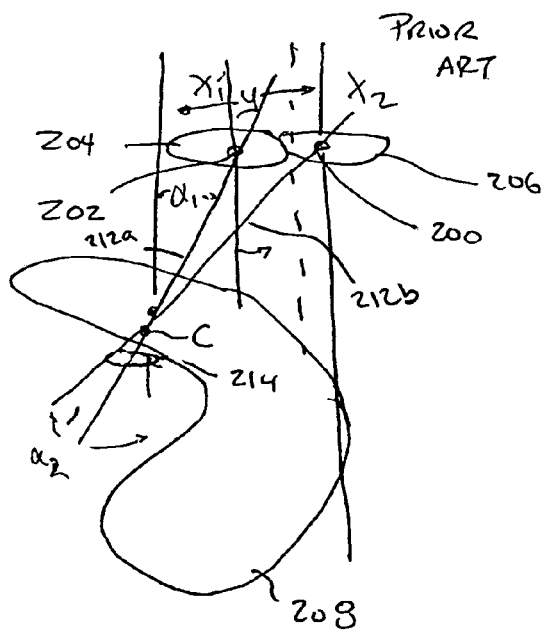
FIG. 14 is a side plan view of a prior art guide showing an often encountered problem of missing the pin due to applied torque.

FIG. 14 shows another prior art guide problems schematically with issues created by over-torquing such as with guide 300 of FIG. 13 or other prior art guides. With the insert location 200 moved horizontally to the right from preferred insert location 202 due to anatomical constraints provided between different clavical 204,206 and coracoid 208 relationships as could differ from patient to patient, a rigid drill guide with drill paths 212a,212b must be rotated potentially beyond its limits to accommodate certain individuals. For example, it may rotate up to ¾ y without disengaging from egress point C shown in FIG. 14. Furthermore, by providing a smaller angle of incidence α less than 90 degrees, a magnification in error be observed with pin trajectory. In the illustrated embodiment, the drill path 212b misses the target 214. This could potentially be problematic, at least in some procedures.

For FIG. 14, $x_1$ represents an individual with a straight trajectory and a high incident angle. $x_2$ represents an individual with an offset between points of engagement thereby creating a low incidence angle α and increases the difficulty of drilling. A variable guide 110 as provided by the Applicant's preferred embodiment and other embodiments may relieve much of this stress provided on the illustrated guide and allow for more careful and/or precise drilling.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A drill guide and pin apparatus comprising:
   a drill guide having a drill sleeve and a boring tool, said boring tool operable to provide a drill bore into a bone portion;

a pin operably coupled by an arm to the boring tool, said pin forming a pin bore into the bone portion at angle α in a range of about 30 degrees to about 170 degrees relative to the drill bore with said pin bore intersecting the drill bore at a predetermined position relative to the arm in a drilling configuration; and a wire directable through the drill bore in a wire insertion process; and a catch provided with the pin, said catch extendable through the pin bore, engagable with the wire when removed, and configured to direct the wire through and out the drill bore in a directing process with the catch grabbing the wire with the action of removing the catch from the pin bore, wherein the catch is defined by two arms providing a bore therethrough and a pinch.

2. The drill guide and pin apparatus of claim 1 wherein the catch is integrally connected to the pin.

3. The drill guide and pin apparatus of claim 1 wherein the pinch receives the wire in the directing process.

4. The drill guide and pin apparatus of claim 1 wherein the wire further comprises a wire stop at a terminal end and the catch cooperates with the wire stop during the directing process.

5. The drill guide and pin apparatus of claim 1 wherein the catch further comprises a notch which cooperates with the wire stop during the directing process.

6. The drill guide and pin apparatus of claim 1 wherein the pin terminates in a point, and the catch is internal to two arms of the pin meeting at a juncture.

7. The drill guide and pin apparatus of claim 1 wherein the boring tool is a drill and the drill passes through a portion of the pin when forming the drill bore.

8. The drill guide and pin apparatus of claim 1 wherein the pin is directed through a pin sleeve.

9. The drill guide and pin apparatus of claim 1 wherein the pin bore is created by directing the pin to a pin depth and stopping the pin at a desired location with a stop.

10. The drill guide and pin apparatus of claim 1 wherein the arm is an adjustable arm and has an adjustable configuration and a locked configuration wherein the pin is movable in at least one plane relative to the drill sleeve.

11. The drill guide and pin apparatus of claim 1 wherein the arm comprises an articulated column.

12. The drill guide and pin apparatus of claim 1 wherein the angle α is between 45 and 135 degrees.

13. The drill guide and pin apparatus of claim 1 wherein the boring tool is a drill having a bore therethrough and the wire is directed through the bore in the drill in the insertion process.

14. A drill guide and pin apparatus comprising:

a drill guide having a drill sleeve and a boring tool, said boring tool operable to provide a drill bore into a bone portion;

a pin directable through a pin sleeve and operably coupled by an arm to the boring tool, said pin forming a pin bore into the bone portion at angle α in a range of about 30 degrees to about 170 degrees relative to the drill bore with said pin bore intersecting the drill bore at a predetermined position relative to the drill sleeve in a drilling configuration; and a wire directable through the drill bore in a wire insertion process; and a catch connected to the pin movably forming the pin bore and engagable with the wire when removed, and configured to direct the wire through and out the drill bore in a directing process with the catch grabbing the wire with the action of removing the catch from the pin bore, wherein the catch is defined by two arms providing a bore therethrough and a pinch.

15. The drill guide and pin apparatus of claim 14 wherein the angle α is between 45 and 135 degrees.

16. The drill guide and pin apparatus of claim 14 wherein the pinch receives the wire in the directing process.

17. The drill guide and pin apparatus of claim 14 wherein the wire further comprises a wire stop at a terminal end and the catch cooperates with the wire stop during the directing process.

18. The drill guide and pin apparatus of claim 14 wherein the boring tool is a drill and the drill passes through a portion of the pin when forming the drill bore.

19. The drill guide and pin apparatus of claim 14 wherein the pin bore is created by directing the pin to a pin depth and stopping the pin at a desired location with a stop.

20. The drill guide and pin apparatus of claim 14 wherein the arm is an adjustable arm and has an adjustable configuration and a locked configuration wherein the pin is movable in at least one plane relative to the drill sleeve.

\* \* \* \* \*